United States Patent [19]

Benedikt

[11] 4,083,949

[45] Apr. 11, 1978

[54] NEW ORAL FORM OF MEDICAMENT AND A METHOD FOR PRODUCING IT

[75] Inventor: Gerald Benedikt, Constance, Germany

[73] Assignee: Byk Gulden Lomberg Chemische Fabrik GmbH, Constance, Germany

[21] Appl. No.: 486,432

[22] Filed: Jul. 8, 1974

[30] Foreign Application Priority Data

Jul. 17, 1973 Germany .............. 2336218

[51] Int. Cl.² .................. A61K 9/22; A61K 9/36
[52] U.S. Cl. .................. 424/19; 424/20; 424/35
[58] Field of Search .................. 424/19–22, 424/32–35; 106/196, 170; 210/500

[56] References Cited

U.S. PATENT DOCUMENTS

| | | | |
|---|---|---|---|
| 2,921,883 | 1/1960 | Reese et al. .............. | 424/20 |
| 3,247,066 | 4/1966 | Milosovich .............. | 424/35 |
| 3,538,214 | 11/1970 | Polli et al. .............. | 424/19 |
| 3,567,809 | 3/1971 | Ueno et al. .............. | 210/500 X |
| 3,593,855 | 7/1971 | Stana .............. | 210/500 |
| 3,648,845 | 3/1972 | Riley .............. | 210/500 X |
| 3,673,084 | 6/1972 | King .............. | 210/500 X |
| 3,780,147 | 12/1973 | Stana .............. | 210/500 X |
| 3,835,221 | 9/1974 | Fulberth et al. .............. | 424/20 |

OTHER PUBLICATIONS

Chem. Abstr. 73#112917t (1970), 74#15708p, #67658s (1971), 75#403474, #91288n (1971) 76#103710e (1972), 77#39139s (1972), 78#164048h (1973), 80#124685y, #100210p (1974), 81#68524b, #82333v, #82334w (1974).

*Primary Examiner*—Shep K. Rose
*Attorney, Agent, or Firm*—Berman, Aisenberg & Platt

[57] ABSTRACT

An oral form of medicament releases active substance in the gastrointestinal tract at a constant rate.

15 Claims, No Drawings

NEW ORAL FORM OF MEDICAMENT AND A METHOD FOR PRODUCING IT

BACKGROUND

Soliva and Speiser [*Pharmaceutica Acta Helvetivae,* 41, 176 to 191 (1966)] discussed the general and biokinetic aspects of peroral depot medication and followed theoretical considerations to the conclusion that, in the case of an ideal depot-form of medicament, the release of active substance should occur at a constant rate, i.e. in accord with a reaction of zero order.

To solve the problem, Lehmann and Dreher [*Pharm. Ind.,* 31, 319 to 322 and 409 to 412 (1969)] proposed the production of tablets with a porous matrix, which were to be provided with a thin permeable Eudragit retard lacquer coating*. The method suffers, however, from the disadvantage that the release of active substance depends on the viscosity of the matrix, on the quantity of matrix, on the specific surface area of the tablets, on the pressing pressure and on the quantity of Eudragit. Dependence on so many factors makes production of such tablets (with a constant active-substance-release rate) a complicated problem. Furthermore, release of active substance does not remain constant if the matrix tablets are subjected to a mechanical load, such as that which occurs in the gastrointestinal tract.

Lehmann [*Pharma International* (1971), No. 3, 34 to 41] suggested adapting the permeability of employed coating materials to suit the solubility properties of the active substances involved. In accordance with this suggestion and by using a combination of insoluble Eudragit retard with types of Eudragit* soluble in the gut, it is possible to vary the permeability of a coating for medicament, which comprises a weakly basic active substance, in accordance with the milieu, i.e. the permeability of the coating increases at that instant in which the coated medicament enters the gut and the solubility of the active substance decreases. The proposal, however, has the disadvantage that the release of active substance cannot be precisely controlled over wide ranges, since (in the case of higher amounts of Eudragit lacquers soluble in the small intestine) the dialysis membrane formed of insoluble Eudragit retard lacquer decomposes. Thus mixing ratios of over 60% by weight of soluble Eudragit lacquer and under 40% by weight of insoluble Eudragit retard lacquer do not lead to any satisfactory results. For example a dialysis membrane made up of 50% by weight of Eudragit retard and 50% by weight of Eudragit soluble in the small intestine completely decomposes at a pH-value of 6 to 7 after 4 hours at the most. Increasing the amount of material soluble in the small intestine to 60% by weight results in a dialysis membrane which decomposes within one hour in artificial intestine juice having a pH-value of 7.3.

These polymeric lacquer substances, based on an acrylate and on a 
* These polymeric lacquer substances, based on an acrylate and on a methacrylate, respectively, are described in "Lexikon der Hilfsstoffe für Pharmazie, Kosmetik und augrluzlude Gebiete" [Editio Cantor KG] by H. P. Fiedler on pages 202 and 203 and in the "Eudragit" brochure of Messrs. Röhm and Haas (1967).

German patent specification (Offenlegungsschrift) No. 2,010,416 (corresponding to U.S. Pat. No. 3,835,221) suggests the production of an oral form of medicament with a retarding action in which the active material is applied to indifferent vehicle balls or spherulets which are then coated with a resorption delaying coating of polyvinyl acetate, preferably in admixture with ethylcellulose. The polyvinyl acetate used has a k-value [determined in accordance with the method of Fikentscher, *Cellulose,* 13, 18 (1932)] of from 20 to 40, and the ethylcellulose used has an ethoxyl content of from 44 to 49.9 at a viscosity between 7 to 100 cp. Such method, however, is limited to active substances which are equally soluble throughout the entire digestive tract.

German patent specification (Offenlegungsschrift) No. 2,148,391 describes a mixture of approximately 90% by weight of cellulose acetate-phthalate and approximately 10% by weight of ethylcellulose, inter alia, as a binding agent (for particles, pressed to form tablets, of 150 microns in diameter) and a calcium or magnesium salt of a higher fatty acid as a barrier agent. The barrier agent delays the penetration of liquids into the interior of the tablets and thus prevents release of the active substance. A drawback of this method, however, is that release of the active substance is only very approximately linear (see example 3 of the noted German patent specification). Furthermore, the use of the barrier agents does not provide for any exact control of the release of the active substance based on the pH-value.

German patent specifications (Patentschriften) Nos. 1,467,781 and 1,467,786 describe dragées with a retarded release of medicament. These dragées consist of pressed pulps containing from 50 to 500% by weight of a swelling agent and from 10 to 50% by weight of a water-insoluble polyvinyl-acetate or a film-forming cellulose acetate-phthalate, the content of swelling agent and of polymers being fixed in relation to the active constituent of the pulp. Illustrative of the swelling agents mentioned are cellulose ethers, such as carboxymethylcellulose, oxyethylcellulose and methyl-cellulose.

A disadvantage of this retard form is that the active drug constituent is not released with constant speed in either artificial digestive fluids or in the gastrointestinal tract. This can readily be seen from example 3 of the '781 patent, which shows the considerable tolerances of the release rate. When the medicament is, e.g., a dragée, it will be intact in the stomach at one instant, but whether the dragée will remain in the stomach or leave it during the next emptying of the stomach is uncertain. Therefore medicament release depends on factors which are hard to control. A further disadvantage is that medicament release within specified tolerances is only achieved with a very large portion of auxiliary substances.

The swelling cellulose ethers used are high-molecular-weight substances which have a viscosity of about 1000 centipoises (cp) (cf. examples 1 to 4 of German specification '781 and examples of German specification '786) and swell in water to form a gel.

SUMMARY OF THE INVENTION

The invention is in an oral depot medicament form which comprises active-substance-containing spheroidal particles provided with a dialysis membrane, whose film former comprises (a) a cellulose ether which is insoluble in the pH range of the gastrointestinal tract and which cannot be enzymatically degraded and (b) one or more organic compounds which are essentially only soluble in the alkaline part of the intestinal tract. The active-substance-containing spheroidal particles are preferably collected together to form a unit dosage.

The aim of the present invention is the provision of (1) an oral medicament form which avoids the limitations, drawbacks and disadvantages of prior-art counterparts, (2) an oral medicament form which releases active substance in the gastrointestinal tract at a constant rate, and 3) a method for producing such oral medicament form.

DETAILS

The cellulose ethers used are rather low-molecular-weight polymers which do not swell to form a gel in an aqueous medium, which have an alkoxy group content of from 43 to 50% by weight and which have a viscosity of from about 7 to 100 cp. Methyl, ethyl and propylcelluloses are particularly preferred.

The viscosity data refer to solutions of cellulose ethers containing 5% by weight of cellulose ether in toluene : ethanol mixtures (80 : 20 parts by weight) measured at 25° C.

In accordance with the invention the cellulose ether solutions with a relatively low viscosity range, i.e. from about 7 to 20 cp. are particularly preferred. But cellulose ether solutions with a higher viscosity range can also be employed. In this case it can be advantageous to dilute the cellulose ether solution with an appropiate solvent.

The organic compounds, substantially only soluble in the alkaline part of the intestinal tract, are characterized by a content of from 5 to 40% by weight of free carboxyl groups. Such compounds are, in what follows, referred to for short as alkali-soluble compounds. Examples of such compounds are, inter alia, natural resins (such as shellac, sandarac, collophonium and copal resins) and artificial resins (such as partially or half esterified maleic anhydride copolymers, more particularly methylvinylethermaleic anhydride copolymers, ethylene-maleic anhydride copolymers, methyl, ethyl, n-butyl, isobutyl and 2-ethylhexyl esters of maleic anhydride copolymers and, furthermore, partial mixed polycarboxylic acid anhydrides or cellulose mixed anhydrides of lower aliphatic monocarboxylic acids, including such esters as those derived from the combination of a single aromatic-nucleus-containing aromatic polycarboxylic acid and a lower aliphatic acid).

Typical cellulose esters with lower aliphatic monocarboxylic acids and with a single aromatic-nucleus-containing aromatic polycarboxylic acid encompass, as aliphatic monocarboxylic acid residues the residues of the 2- to 4-carbon atom-containing saturated aliphatic monocarboxylic acids, such as of acetic, propionic or butyric acid. Suitable single aromatic-nucleus-containing polycarboxylic acids are the 8 carbon atom containing aromatic dicarboxylic acids, such as phthalic and isophthalic acid or mixtures thereof.

Preferred materials of this type are partial esters and semi-esters of cellulose butyrate-phthalate, cellulose acetatephthalate, cellulose propionate-phthalate and hydroxypropylmethyl cellulose phthalate.

A typical product suitable as film former in accordance with the present invention is CAP (cellulose acetate-phthalate) sold by Eastman Kodak. This product is characterised in that it contains on the average, about 1.5 hydroxyl groups per monomer unit of cellulose (=glucose) esterified with acetic acid and about 0.7 to 0.8 hydroxyl group per monomer unit esterified with phthalic acid. The second carboxylic acid group of partially esterified phthalic acid is a free carboxylic acid group (—COOH), capable of forming a salt with organic and inorganic bases. Therefore CAP is soluble over a pH range of about 6.5 and above.

Cellulose propionate-phthalate and cellulose butyrate-phthalate have similar structural units as CAP, with the only difference the acetic acid units of CAP being replaced by propionic or butyric acid, respectively.

Hydroxypropylmethyl cellulose phthalate is a reaction product of hydroxypropylmethyl cellulose with phthalic acid or phthalic acid anhydride.

A typical hydroxypropylmethyl cellulose phthalate is HP (abbreviation for HPMCP), described in the HP brochure of Messrs. Shinetsu, Tokyo and sold in different specifications, such as HP 45, HP 50 and HP 55, the numbers 45, 50 and 55 indicating the pH values 4.5, 5.0 and 5.5 respectively, at which the corresponding HP lacquer goes into solution.

Other compounds soluble in the alkaline range and suitable for the production of the new forms of medicament are represented by higher fatty acids, for example stearic acid, with a melting point above 30° C.

The film-forming component of the dialysis membrane comprises (according to the particular active substance used) from 15 to 70% by weight of cellulose ether and from 30 to 85% by weight of the alkali-soluble compound.

The table on the following page enumerates preferred alkali-soluble compounds together with their physical characteristics, their content of free carboxyl groups and their preferred proportion by weight in the novel dialysis membranes; see H. P. Fiedler, "Lexikon der Hilfsstoffe für Pharmazie, Kosmetik und angrenzende Gebiete," Editio Cantor KG (1971).

The incorporation of the compound (which is water-soluble in the alkaline range and is water-insoluble in the acidic range) into the dialysis membrane of the medicament form makes precise control of the release of active substance possible, since permeability of the dialysis membrane is adapted in each respective case to the solubility of the active substance in the individual ranges of the gastrointestinal tract. Very many medicaments are salts of weak bases. Such substances have excellent solubility in the acidic range; however, in the neutral or alkaline range the solubility of these materials decreases by several powers of 10, i.e. several orders of magnitude. The concentration of active substance within the dialysis membrane for these medicaments is substantially greater in the acidic range of the stomach than in the alkaline range of the intestine. The concentration gradient of the drug constituent often changes to a great extent during passage of a medicament form through the stomach and intestine. However, since the permeability of the subject dialysis membrane adapts itself to the respective and changing pH-range during passage through the stomach and intestine, variations in the concentration gradient are compensated for accordingly and essentially the same quantity of active substance is released per unit time during the whole passage through the stomach and intestine. In the acidic range of the stomach the concentration gradient of a weakly basic medicinal substance is admittedly high in the novel dialysis membrane, but the permeability of the membrane is low. Although the concentration gradient in the membrane decreases in the alkaline intestinal tract owing to decreased solubility of the active substance, the alkaline-soluble component of the membrane dissolves and the permeability of the membrane is increased at the same time.

TABLE

Preferred alkali-soluble compounds

| Compound | Viscosity or melting point respectively | Carboxyl group Content (percentage by weight) | Amount by weight of dialysis membrane (percentage by weight) |
|---|---|---|---|
| (1) cellulose acetate-phthalate | 70–80 cp (10% in acetone, 20° C) | 9 – 13% | 30 – 85% |
| (2) hydroxypropylmethyl cellulose phthalate | 450±90 cp (15% in acetone: ethanol 1:1, 20° C) | 6 – 8% | 30 – 85% |
| (3) hydroxypropylmethyl cellulose phthalate | 150±30 cp (15% in acetone: ethanol 1:1, 20° C) | 8 – 12% | 30 – 85% |
| (4) shellac | 115° – 120° C | 8 – 10% | 30 – 85% |
| (5) sandarac | 135° C | — | 30 – 85% |
| (6) methacrylic acid-methacrylic acid ester copolymer | — | 36 – 37% | 30 – 85% |
| (7) methacrylic acid-methacrylic acid ester copolymer | — | 22 – 23% | 30 – 85% |
| (8) ethyl ester of poly(methylvinylether/maleic acid) | — | 34 – 40% | 20 – 85%* |
| (9) stearic acid | 71° C | 16% | 15 – 40%* |
| (10) palmitic acid | 62° C | 18% | 15 – 40%* |
| (11) myristic acid | 54° C | 20% | 15 – 40%* |

*Note: This alkali-soluble compound is preferably used in combination with one or more other alkali-soluble compounds listed in this table.

Since the different medicinal substances have very different solubility characteristics during passage through the gastrointestinal tract, it is not possible to specify any weight ratio of dialysis membrane former (cellulose ether + alkali-soluble compound) to medicinal substance which is applicable for all medicinal substances. A man of ordinary skill in the art can, however, readily determine this weight ratio on the basis of simple tests from the release of active substance in accordance with the half-change method of the USP-decomposition tester and in accordance with the half-change method using the Sartorius solubility model of H. Stricker with mechanical loading. For the dialysis membranes of this invention the proportion by weight of alkali-soluble compound must be made to increase with an increase in the difference of the solubilities between stomach and intestine) of a medicinal substance. However, since the weight ratio of cellulose ether to alkali-soluble compound can be varied within wide limits while still obtaining the dialysis membrane, the novel retarding form of medicament is of universal application. The novel dialysis membrane still remains intact under mechanical loading if it consists of up to 85% by weight of compounds soluble in the small intestine. This weight ratio is necessary in the case of large differences in solubility of the active substance in the acidic and alkaline ranges of the gastrointestinal tract. This surprising stability is not possessed by previously-proposed dialysis membranes.

The new method of retarding resorption is particularly suitable for the processing in the whole gastrointestinal tract of readily-soluble active substances and of active substances which are sparingly soluble in the neutral to alkaline intestinal range. Readily-soluble active substances, for example readily soluble salts of organic acids [for example readily-soluble salts of salicylic acid and, more particularly, sodium salicylate (solubility: 110 g in 100 ml of water at 20° C)] and salts of weak organic bases [for example dextropropoxyphene . HCl] with large differences of solubility in acidic and alkaline parts of the gastrointestinal tract (solubility at pH 2 and 20° C above 50 g per 100 ml of water, at pH 7 and 20° C below 1 g per 100 ml of water) can be prepared to form depot preparations with an even active-substance release over a period of up to 10 hours. Accordingly, preferred forms of medicament of the invention are characterized by an active substance which is a nitrogen-containing organic base or a salt of such a base, with a $pK_B$-value of the base below 14. The $pK_B$-value can be derived from the reaction equation $$B + H_2O \rightleftarrows BH^+ + OH^-$$

from the law of mass action,

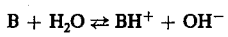

$B$ ... base
$BH^+$ ... corresponding cation acid $$K_B = \frac{[BH^+][OH^-]}{[B]}$$

and from $$pK_B = -\log_{10} K_B.$$

In particular the $pK_B$-values of the prepared active substances lie between 5 and 14. Examples for these active substances are alkaloids, e.g. dihydroergotamine, papaveridine, codeine, noscapine hydrochloride and alkaloid-like substances. e.g. ethylephrine.

Furthermore, the novel depot forms of medicament comprise medicaments which have a quotient of the solubility in the stomach to that in the alkaline intestinal tract of from 2 to 1 up to 1500 to 1.

The spheroidal particles (preferably united together to form a unit dosage), comprising active substance provided with a dialysis membrane, of the instant medicament form have any desired size. They are, e.g., in the form of large powder particles, in the form of large crystals of a spheroidal form, in the form of rounded granules [for their preparation see *Pharm. Ind.*, 31, 319 to 322 (1969)] or in the form of small beads, so-called pellets. In accordance with the invention pellets, whose size lies between 0.1 and 2 mm in diameter and preferably between 0.8 and 1.6 mm in diameter, are preferred. By using pellets of a size which is as uniform as possible, a particularly even release of active substance is obtained.

The particles, making up the novel form of medicament can have an active substance content of up to 90% by weight if high doses of the active substance are appropriate. In the case of lower doses of the active substance the particles comprise up to 80% by weight of vehicle materials.

The new film-forming coating can, but need not necessarily, comprise conventional adjuvants, for example plasticizers, wetting agents and dyes. Plasticizers are necessary, e.g., when synthetic or natural polymeric materials, which are soluble in the small intestine, are employed. Suitable pharmacologically-compatible plasticizers are, for example, to be found in the series of phthalic acid, phosphoric acid, citric acid and glyceric acid esters. When fatty acids with a melting point of above 30° C are used as alkali-soluble compounds, no plasticizer is necessary. Wetting agents are needed when the coating is to be colored with coloring lacquers; sorbitan fatty acid esters or salts of dioctylsulfosuccinic acid are suitable wetting agents in such event.

The new particles provided with a dialysis membrane and with a delayed release of active substance can also be administered directly, for example with a spoon, but generally a unit containing the desired dose is pre-fabricated.

The preferred form of medicaments (according to the invention) are tablets; capsules, which are made up of the spheroidal particles provided with the novel dialysis membrane and comprising the active substance, are particularly preferred.

The present invention includes a method for the production of the novel depot form of medicament and the dialysis membranes which constitute an essential part of such form. The method is characterized by providing conventionally-produced spheroidal medicament particles (during or after preparation) with a dialysis membrane which, as a film former, comprises 15 to 70% by weight of a cellulose ether with an alkoxy group content of 43 to 50% by weight and a viscosity of about 7 to 100 cp and 85 to 30% by weight of a material which is soluble in the alkaline range of the intestinal tract; the particles of medicament provided with the dialysis membrane are optionally converted in a conventional manner into dosing or dosage units. It is possible to apply both film formers in separate coating procedures to the spheroidal medicament particles but is is also possible to use a mixture of the cellulose ether with a material which is soluble in the alkaline range of the intestinal tract as a film former.

For the selection of the film-forming components preferred in accordance with the present invention attention is drawn to the preceding description. In what follows the individual method steps are discussed.

(1) PRODUCTION OF THE MEDICAMENT PARTICLES

For medium and low dosages the medicament is, e.g., applied to spheroidal vehicle particles, such as homeopathic spreading spherulets, while for higher medicament dosages medicament crystals are optionally used in place of vehicle particles to make a reduction in the amount (by weight) of carrying or vehicle materials possible. Medicament pellets produced with an active substance content of up to 90% by weight in accordance with the Merumeriza Method [see A. D. Reynolds, *Manufacturing Chemist and Aerosol News*, 41, 40 to 43 (1970)] are alternatively employed.

The application of the active substance on inert spherulets as a vehicle is carried out in the presence of an adhesive. Illustrative adhesives include natural or synthetic materials and, in particular, gelatine solutions, starch paste, soluble starch, sugar or glucose sirup, Guar gum solutions, carrageen, alginic acid, cellulose ethers (for example methyl, hydroxyethyl, ethyl and ethylhydroxyethyl cellulose ether solutions), polyvinylpyrrolidone, bentonites, courlose or manioc paste. The active substance is usually applied in a finely pulverulant form, often in the presence of pulverulant adjuvants, on the inert vehicle spherulets. The pulverulant adjuvants are present, e.g., in amounts equal to from 5 to 80% of the weight of the active substance. The dragée-forming operation is repeated as often as desired. If the retarded medicament is a base it is convenient to add to it a galenically compatible acid, with which the medicament forms a moderately-soluble salt; this medicament/acid mixture can be applied to the vehicle spherulets. The addition of acid advantageously reduces the solubility of the medicament in gastric juice so that the concentration difference of the active substance within the membrane is not as large on passing into the small intestine.

In the production of medicament particles care should be taken to see that they have the most uniform size possible in order to enable an application of the film-forming components which is as even as possible. It is possible to proceed in accordance with a preferred form of the method in such a manner that the vehicle spherulets of sugar, lactose or maize starch of a diameter of, preferable, approximately 1 mm are evenly moistened with an alcoholic ethyl cellulose solution and are mixed with a medicament/talc mixture until the spherulets roll again freely. After drying, the operation is repeated until all of the active substance has been applied. This method has the advantage that medicament spherulets are produced with a particularly high degree of stability as regards mechanical loading, and they keep their external shape even after all of the active substance is diffused out of them. Owing to the low mechanical self-deformation of the obtained spherulets, the later applied dialysis membrane is hardly damaged even under application of considerable mechanical loads.

The medicinal substance is optionally dissolved or dispersed in the adhesive before applying the resulting solution or suspension evenly to the particle surface.

(2) APPLICATION OF THE DIALYSIS MEMBRANE TO THE MEDICINAL SUBSTANCE SPHERULETS

The application of the dialysis membrane to the medicinal substance spherulets is carried out by conventional methods. It is, however, advantageous to use coating methods which are capable of producing most uniform application of the dialysis membrane. Therefore, use is generally made of solutions for the two film formers. As solvents for the two components low-boiling-point organic solvents are generally suitable. Particularly suitable are lower alcohols, such as lower alkanols, e.g. methanol, ethanol and isopropanol; low-boiling-point halogenated hydrocarbons, such as lower haloalkanes, e.g. methylene chloride; low-boiling-point ketones, such as lower alkyl and cycloalkyl ketones, e.g. acetone, ethylmethylketone and cyclohexanone; low-boiling-point esters, such as lower alkyl esters of lower alkanoic acids, e.g. methyl acetate and ethyl acetate; aromatic hydrocarbons, e.g. benzene; and mixtures of these materials.

The lacquer solution forming the dialysis membrane is, according to a preferred embodiment of the method, applied (with the help of a spraying device) in a finely divided form on the surface of the medicament spherulets. This operation is, e.g., carried out in a rapidly rotating dragée-making vessel, though it is better to use a fluidized bed method. In this respect the solvent and the geometry of the spraying device can be so selected that the solvent evaporates on impinging on the surface of the medicament particles. In this manner it is possible to obtain a continuous application of the dialysis membrane without intermediately dispersed drying stages.

In the case of a low dosage of the medicaments it is possible to combine the method steps (1) and (2) and to distribute the medicament with talc in the retarding lacquer solution and to spray this suspension in the fluidized bed method on to the vehicle spherulets.

If thus-obtained medicament particles (provided with the novel dialysis membrane having a delayed release of active substance) are not administered directly to the patient (something which is possible with medicaments with a wide therapeutic spectrum), the novel medicament particles are packed together in a unit dosage in a further method step.

(3) METHODS FOR PRODUCTION OF CAPSULES, TABLETS, ETC.

The coated medicament particles are conveniently filled into capsules which are preferably of the telescoping gelatine type. For dosing, the medicament particles are either weighed out or dispensed with dispensing tongs or filling devices and filled with capsule filling devices into the capsules, the latter then being sealed.

The new medicament particles are, however, alternatively mixed with other pharmaceutical adjuvants and pressed to form tablets. This is suitable for medicament particles with a diameter of up to 1 mm without damage of the dialysis membranes.

The subject method has the further advantage over prior art that, for the production of any desired quota or rate of release, preliminary preparation and admixture of differently designed granule fractions are obviated. Instead, uniform charges are filled into telescoping capsules or pressed in admixture with pharmaceutical adjuvants to form tablets. The weight ratio of cellulose ether to alkali-soluble compound is varied according to the solubility characteristics of the medicament without any change in the method steps within wide limits.

The novel depot medicament forms make rapid achievement of therapeutic blood level values possible, ensure a constant blood level over a desired period of time, lead to uniform and persistant biological action and reduce undesired side-effects by avoiding peaks or surges in concentration. The new principle of retardation is suitable, for example, for the production of retard forms of tranquilizers, diuretics, sedatives, antibiotics, vitamins, analgesics, blood pressure lowering preparations, hormones, psychopharmic preparations and anticoagulants. For example, the following active substances are readily prepared in such depot forms of medicaments: 1,2-dimethyl-4-{γ-[4'-(o-methoxyphenyl)] piperazinyl-(1)-propylamino}uracil, dextropropoxyphene-hydrochloride, sodium salicylate, 1-(p-chlorophenyl)-2,3-dimethyl-4-dimethylaminobutanol-(2)-hydrochloride, dextroamphetamine sulfate, 1-phenyl-1-(2-pyridyl)-3-dimethylaminopropane hydrogen-maleinate, 1-(2-phenylethyl)biguanide-hydrochloride, trifluoperazine-dihydrochloride, chlorophenamine maleate and D,L-2-amino-1-(4-hydroxyphenyl)-ethanol-hydrochloride.

This new form of medicament is preferably administered in combination with an initial dose of the medicament. A certain initial dose is also provided by the oral depot form of medicament in accordance with the invention; the initial dose is due to the fact that the dialysis membrane of the medicament form only releases medicament at a constant rate in a slightly swollen condition. Before swelling equilibrium is achieved (something which occurs quickly), a higher rate of active-substance release initially occurs (something which is desired since it results in administration of an initial dose). After equilibrium has been achieved, release of active substance generally occurs in accordance with a reaction of zero order.

The subject oral medicament form is equally suitable for the preparation of combinations of active ingredients contained therein. If the active ingredients have approximately the same solubility characteristics and are chemically and physiologically compatible, pellets containing the combined active substances can be prepared and coated with the retard lacquer as described above.

In case of different solubility characteristics of the active ingredients employed another procedure has to be followed. In accordance with the preceding description for each active substance desired for the combination, the weight ratio of dialysis membrane former (cellulose ether + alkali-soluble compound) to medicinal substance is determined in accordance with the half-change method of the USP-decomposition tester and in accordance with the half-change method using the Sartorius solubility model of H. Stricker with mechanical loading. Having determined this weight ratio for each medicinal substance separately, different kinds of pellets for each medicinal substance are prepared, are coated with different amounts of dialysis membrane former corresponding to the weight ratio determined for each medicinal substance.

These different kinds of pellets can be conveniently packed together in a unit dosage as described above.

The active ingredients or combinations thereof are administered in the same manner (orally), in essentially the same amounts, according to essentially the same schedules and for the same purposes as such ingredients in other oral dosage forms. In view of the uniform rate of release in the gastrointestinal tract, smaller amounts of any particular medicament may well establish and maintain a given blood level of the medicament over the same or a longer period of time.

The invention and its advantages are readily understood from the preceding description. It is apparent that various changes can be made in the process, in the dialysis membrane and in the ultimate oral medicament form without departing from the spirit and scope of the invention or sacrificing its material advantages. The process and products hereinbefore described and those illustrated in the following examples are merely illustrative embodiments of the invention.

EXAMPLE 1

BLOOD-PRESSURE-LOWERING PREPARATION IN RETARD FORM 7 kg of sugar spherulets with an average diameter of 0.8 mm are evenly moistened in a rotating dragee-making vessel with approximately 300 g of a 10% ethanolic ethyl cellulose solution having a viscosity of 10 cp at 25° C and an ethoxyl-group content of 48 to 49.5% by weight. Following this 400 g of a finely pulverized mixture of

| | |
|---|---|
| 1,2-dimethyl-4-{γ-[4'-(o-methoxyphenyl)]piperazinyl-(1)-propylamino}uracil (Urapidil) | 12.00 kg |
| fumaric acid | 4.00 kg |
| talc | 3.00 kg | is applied to the moistened spherulets and dried with air from a blower. The operation is repeated until the whole mixture of active substance has been applied. For this purpose 15 kg of the above used 10% ethanolic ethyl cellulose solution are required. The active substance pellets so produced have a size between 1.4 and 1.6 mm and comprise Urapidil equal to 56% of their weight.

These pellets are sprayed in a fluidized bed apparatus with a solution of 350 g of the above used ethyl cellulose (with an ethoxyl-group content of 48 to 49.5% by weight) and 350 g of stearic acid in 12 liters (1) of dichloromethane.

The release of active substance, as determined by the half-change method in the USP decomposition tester, leads to the following values:
 1 h: 14.9%
 2 h: 25.3%
 3 h: 33.0%
 4 h: 43.8%
 5 h: 53.7%
 6 h: 62.8%
 7 h: 73.7%
 8 h: 85.4%
 9 h: 92.0%

The release of active substance as determined by the halfchange method in the Sartorius solution model in accordance with H. Stricker (with a mechanical loading) yields practically identical values:
 1 h: 16.3%
 2 h: 28.4%
 3 h: 40.4%
 4 h: 48.4%
 5 h: 55.8%
 6 h: 64.1%
 7 h: 72.0%
 8 h: 79.0%
 9 h: 87.0%

After a storage time of 3 months at 40° and 50° C the release of active substance does not change. Furthermore, the external appearance is not changed by such storage.

The material, corresponding to an active substance content of 90 mg, is filled into a size-3 capsule.

When one capsule is administered to adult humans each 12 hours a constant blood level and a satisfactory blood pressure lowering action is achieved.

When the same pellets are coated according to prior art with a commercially available acrylic acid polymer [Eudragit retard S and Eudragit retard L 1:1], the following results are achieved:

For an amount of lacqeur which is 3.4% by weight of the pellets the release values are:
 1 h: 38.0%
 2 h: 62.0%
 3 h: 73.0%
 4 h: 77.5%
 5 h: 82.5%
 6 h: 85.0%
 7 h: 87.0%
 8 h: 88.5%

For an amount of lacquer which is 6.2% of the weight of the pellets the following release values are obtained:
 1 h: 20.0%
 2 h: 45.0%
 3 h: 55.0%
 4 h: 61.0%
 5 h: 65.0%
 6 h: 68.0%
 7 h: 70.5%
 8 h: 73.0%

As can be seen, the release occurs with decreasing installments, i.e. at a decreasing rate, so that with such a preparation an even blood level cannot be obtained.

EXAMPLE 2

The pellets produced according to example 1 are sprayed with the following solution:

| | |
|---|---|
| ethyl cellulose (10 % ethanolic solution, 10 cp) (ethoxyl-group content of 48 to 49.5 % by weight) | 250 g |
| Carboxyl-group-containing acrylic acid polymer in the form of Eudragit L (polycarboxylic acid ester with a carboxyl group content of approximately 26 % by weight) | 250 g |
| diethyl phthalate | 40 g |
| magnesium stearate | 250 g |

A mixture of 7 l of dichloromethane and 7 l of denatured ethanol is used as solvent for the solution.

The release figures, as determined by the methods described in Example 1, are as follows:
 1 h: 22%
 2 h: 38%
 3 h: 53%
 4 h: 65%
 5 h: 78%
 6 h: 92%
 7 h: 100%

As compared with Example 1, the release occurs in larger but very even installments.

When 200 g of acrylic acid polymers (with a carboxyl-group content of 34 to 40% by weight in the form of Eudragit L) are used with 300 g of ethyl cellulose (as described in the foregoing example) as film former, satisfactory dialysis membranes are also obtained.

EXAMPLE 3

Retard Form of an Analgesic Medicament 14 kg of sugar spherulets with a diameter of 0.6 mm are evenly moistened in a rotating dragée-forming vessel with approximately 500 g of a 10% ethanolic ethyl cellulose solution (ethoxyl content of 45 to 46%, 10 cp) and, following this, 500 g of finely powdered sodium salicylate are applied to the thus-moistened spherulets. This operation is repeated until 38 kg of sodium salicylate have been applied. For this purpose 30 kg of the above described 10% ethanolic ethyl cellulose solution are used. The size of the active substance pellets so produced lies between 1.4 and 1.6 mm, and they comprise an amount of sodium salicylate equal to 84% of their weight.

These pellets are sprayed in a fluidized bed apparatus with a solution of 3.8 kg of shellac (with a carboxyl group content of 6% by weight) and 700 g of ethyl cellulose (having a viscosity of 10 cp in 10% ethanolic solution and an ethoxy-group content of about 48 to 49.5% by weight) in a mixture made up of 38 l of denatured ethanol and 38 l of dichloromethane.

The active substance release figures, as determined according to the half-change method, are as follows:
 1 h: 25.6%
 2 h: 40.8%
 3 h: 55.3%
 4 h: 65.1%
 5 h: 83.2%
 6 h: 95.4%
 7 h: 103.5%

The figures for the release of active substance in accordance with the half-change method as determined in the Sartorius solution model of H. Stricker do not depart therefrom by more than ±3%.

COMPARATIVE EXAMPLE 3A

The pellets produced according to Example 3, first paragraph, are sprayed with a solution of 3.8 kg of methacrylic acid-methacrylic acid ester copolymerisate having a carboxyl group content of 36 to 37% (Eudragit L) and 700 g of methacrylic acid-methacrylic acid ester copolymerisate having a carboxyl group content of 22 to 23% (Eudragit S) in 38 l of denatured ethanol and 38 l of dichloromethane.

The active substance release figures, as determined according to the half-change method, are as follows:
1 h: 0%
2 h: 2%
3 h: 100%

These results show that, by the sole application of film formers which are soluble in intestinal juices, the release of active substance readily occurs at or approaching the neutralization point. This medicament form acts as a stomach-resistant form and is not apt to achieve constant blood level values.

EXAMPLE 4

Retard Tablets of Sympathomimetic Medicament 10 kg of sugar spherulets with a diameter of 0.7 to 0.9 mm are sprayed with the following solution in a fluidized bed apparatus (for example WSG 15 of Messrs. Glatt):

| | |
|---|---|
| D,L-2-amino-1-(4-hydroxyphenyl)ethan-1-ol-hydrochloride | 5.000 kg |
| polyvinylpyrrolidone (in the form of Kollidon with a molecular weight of about 25,000) | 0.700 kg |
| sodium pyrosulfite | 0.005 kg |
| distilled water | 5.000 kg |

The air supply temperature is set to 80° to 100° C. After the solution is applied, the pellets of active substance, which have a size of 1.0 to 1.2 mm and an amount of active substance of 30%, are immediately coated with the following solution:

| | |
|---|---|
| ethyl cellulose (ethoxyl content 48 to 49 %, 10 cp) | 500 g |
| hydroxypropylmethyl cellulose phthalate (carboxyl group content of from 8 to 12 %, viscosity of a 15 % by weight solution in acetone-ethanol (1:1) at 20° C=450±90 cp) | 215 g |
| denatured ethanol | 7 l |
| dichloromethane | 7 l |

61,420 Pellets are obtained with an active substance content of 30% by weight.

These pellets are mixed with 10 kg of granulated lactose, 3.2 kg of directly-pressable starch and 380 g of magnesium stearate and pressed to form tablets having a weight of 600 mg and a diameter of 12 mm. These tablets break up in water within 3 minutes and release the active substance pellets.

The active substance release figures, as determined according to the half-change method, are as follows:
1 h: 28.9%
2 h: 40.2%
3 h: 52.2%
4 h: 65.2%
5 h: 84.1%
6 h: 97.6%

EXAMPLE 5

Retard Capsules of an Analgesic Medicament 8.8 kg of sugar spherulets with a diameter of 0.7 to 0.9 mm are moistened in a rotating dragée-making vessel with 300 ml of a 10% ethanolic ethyl cellulose solution (ethoxyl content 48 to 49%, 10 cp), and 300 g of a mixture of 19 kg of dextropropoxyphene-hydrochloride, 4.8 kg of fumaric acid, 4.8 kg of talc and 500 g of aerosil is applied to the thus-moistened spherulets. This operation is repeated until the whole mixture of active substance is similarly applied. 41.2 kg of pellets of the following composition are obtained:

| | |
|---|---|
| dextropropoxyphene hydrochloride | 19.0 kg |
| fumaric acid | 4.8 kg |
| talc | 4.8 kg |
| aerosil 200 (see H.P. Fiedler, Lexikon der Hilfsstoffe, Editio Kantor K.G., 1971, page 20) | 0.5 kg |
| sugar spherulets | 8.8 kg |
| ethyl cellulose (ethoxyl content 48 to 49 %, 10 cp) | 3.3 kg |
| | 41.2 kg |

These pellets are sprayed with a solution of:

| | |
|---|---|
| ethyl cellulose (ethoxyl content 48 to 49%, 10 cp) | 2.20 kg |
| stearic acid | 0.80 kg |
| methacrylic acid-methacrylic acid ester copolymer (acid number 292, Eudragit L) | 0.80 kg | in a mixture made up of 15 l of denatured ethanol and 30 l of dichloromethane in a fluidized bed apparatus. The pellets are filled into hard gelatine capsules of capsule size 1. Each capsule contains 360 mg of pellets corresponding to 150 mg of dextropropoxyphene hydrochloride.

The release rate of active substance, as determined by the half-change method in the decomposition tester according to USP XVII, is found to be as follows:
1 h: 13.6%
2 h: 26.8%
3 h: 37.8%
4 h: 48.7%
5 h: 64.8%
6 h: 79.8%
7 h: 88.8%
8 h: 99.9%

Determination of the release of active substance by the half-change method in the Sartorius solution model of H. Stricker leads to practically identical values.

This linear rate of release is achieved although the difference in solubility of dextropropoxyphene on transition from the acid to the neutral range is approximately 1000 to 1.

The solubility of dextropropoxyphene was found to be as follows: At pH 2 above 50 g per 100 ml, at pH 6.5 0.08 g per 100 ml and at pH 7.5 0.05 g per 100 ml.

EXAMPLE 6

Depot Form of a Bronchodilator 5.19 kg of sugar pellets having a diameter of from 0.5 to 0.6 mm are sprayed in a fluidized bed apparatus with the following suspension:

79.00 kg theophylline
3.96 kg ethylcellulose (ethoxy content 48 to 49%, 10 cp)

11.85 kg polyvinylpyrrolidone (as described in Example 4)
316.00 l denatured ethanol
652.60 l dichloromethane 100 kg of theophylline pellets are obtained having a theophylline content of 79% by weight.

These pellets are sprayed with a retard lacquer solution of the following ingredients:

450 g ethylcellulose (ethoxy content 48 to 49%, 10 cp)
225 g stearic acid
225 g Eudragit L
10 l denatured ethanol
10 l dichloromethane The active-substance release figures (following the half-change method in the USP decomposition tester) are as follows:
1 h: 12.6%
2 h: 26.7%
3 h: 41.5%
4 h: 50.9%
5 h: 61.2%
6 h: 76.3%
7 h: 90.0%
8 h: 98.0%

From the Sartorius model (following the half-change method) almost the same values are obtained:
1 h: 8.9%
2 h: 21.9%
3 h: 40.9%
4 h: 54.9%
5 h: 68.1%
6 h: 81.3%
7 h: 92.0%
8 h: 102.0%

Throughout the specification and claims the following terms are to be understood according to the noted meanings:

dialysis membrane — a membrane coating applied to particles and having a diffusion permeability which varies during passage through the gastrointestinal tract to compensate for changes of medicament (contained in the membrane-coated particles) solubility and to produce milieu-independent medicament release;

homeopathic spreading spherulets — pellets or nonpareilles [types of globuli having a weight of from about 1 to about 500 milligrams (preferably made from saccharose)] used for homeopathic preparations [cf. Gstirner, F., "Einführung in die Verfahrenstechnik der Arzneiformung," fourth edition, pages 394 ff, Wissenschaftliche Verlagsgesellschaft mbH, Stuttgart, 1972];

pressed pulp — a tablet;

Eudragit lacquers L and S are anionic polymerisates of methacrylic acid and methacrylic acid esters. These polymers are only soluble in the alkaline part of the intestinal tract. They are resistant to gastric juice of a pH below 6 and have a free carboxylic-acid-group content ranging from about 20 to 40% by weight.

Whereas Eudragit L is soluble in the neutral pH range above 6 (in duodenal juice), Eudragit S is soluble in a pH range above 7 (in the lower portions of the small intestine).

Both products are further described in the Eudragit brochure of former Messrs. Röhm and Haas (1967), now Messrs. Röhm, where detailed physical-chemical data of these products are given.

What is claimed is:

1. A therapeutically-useful and pharmacologically-acceptable oral depot medicament form comprising substantially uniformly-sized spheroidal medicament particals, each of which is provided with a dialysis membrane and has a diameter of between 0.1 and 2 millimeters, the dialysis membrane having a film-forming component which comprises
   (a) from 15 to 70 percent by weight of a cellulose ether, selected from the group consisting of methyl cellulose, ethyl cellulose and propyl cellulose, which is insoluble in the pH range of the gastrointestinal tract, which is not enzymatically degraded, which has an alkoxy-group content of from 43 to 50 percent by weight, and which has a viscosity of from about 7 to 100 centipoises in a 5 percent by weight toluene-ethanol mixture (80:20 parts by weight) at 25° C and
   (b) from 85 to 30 percent by weight of an organic-compound component which is substantially only soluble in the alkaline pH range of the intestinal tract, which contains from 5 to 40 percent by weight of free carboxyl groups, and which comprises at least one organic compound selected from the group consisting of palmitic acid, myristic acid and stearic acid.

2. A therapeutically-useful and pharmacologically-acceptable oral depot medicament form according to claim 1 wherein the cellulose ether (a) is ethyl cellulose.

3. An oral depot medicament form according to claim 1 comprising readily water-soluble medicament.

4. An oral depot medicament according to claim 1 comprising medicament which is sparingly soluble in neutral to alkaline parts of the intestine.

5. A medicament form according to claim 1 containing active ingredient which
   (a) is a nitrogen-containing base with a $pK_B$-value of from 5 to 14 or a salt of such base or
   (b) has a solubility quotient of from 2:1 to 1500:1 based on its solubility in the stomach divided by that in the intestinal tract.

6. A medicament form according to claim 1, the spheroidal particles of which have a diameter of from 0.8 to 1.6 millimeters.

7. A medicament form according to claim 1, the spheroidal particles of which have a diameter of up to 1 millimeter.

8. A medicament form according to claim 1 in unit dosage form.

9. A medicament form according to claim 8 in capsule form.

10. A tableted therapeutically-useful and pharmacologically-acceptable oral depot medicament form wherein the oral depot medicament form is that of claim 1.

11. A therapeutically-useful and pharmacologically-acceptable oral depot medicament form according to claim 1 and wherein the dialysis membrane consists essentially of (a) and (b).

12. A therapeutically-useful and pharmacologically-acceptable oral depot medicament form according to claim 2 wherein component (b) of the dialysis membrane comprises stearic acid.

13. A therapeutically-useful and pharmacologically-acceptable oral depot medicament form according to claim 2 wherein component (b) of the dialysis membrane comprises palmitic acid.

14. A therapeutically-useful and pharmacologically-acceptable oral depot medicament form according to claim 2 wherein component (b) of the dialysis membrane comprises myristic acid.

15. A therapeutically-useful and pharmacologically-acceptable oral depot medicament form according to claim 1 and wherein the dialysis membrane film-forming component further comprises anionic polymerizate of methacrylic acid and methacrylic acid ester which is soluble in the neutral pH range above 6 and which has a free carboxylic-acid-group content ranging from about 20 to 40 percent by weight.

* * * * *